United States Patent
Yamada

(10) Patent No.: US 10,893,676 B2
(45) Date of Patent: Jan. 19, 2021

(54) 1-ACETYL-3-PHENYL UREA COMPOUND, AND USE THEREOF

(71) Applicant: Sumitomo Chemical Company, Limited, Tokyo (JP)

(72) Inventor: Shinya Yamada, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 144 days.

(21) Appl. No.: 16/328,072

(22) PCT Filed: Aug. 24, 2017

(86) PCT No.: PCT/JP2017/030248
§ 371 (c)(1),
(2) Date: Feb. 25, 2019

(87) PCT Pub. No.: WO2018/038190
PCT Pub. Date: Mar. 1, 2018

(65) Prior Publication Data
US 2019/0174762 A1    Jun. 13, 2019

(30) Foreign Application Priority Data
Aug. 26, 2016  (JP) .................................. 2016-165424

(51) Int. Cl.
*A01N 47/34*     (2006.01)
*C07D 213/69*    (2006.01)

(52) U.S. Cl.
CPC ........... *A01N 47/34* (2013.01); *C07D 213/69* (2013.01)

(58) Field of Classification Search
CPC .............................. C07D 213/69; A01N 47/34
See application file for complete search history.

(56) References Cited

U.S. PATENT DOCUMENTS

| 2,762,696 A | 9/1956 | Gerjovich et al. |
| 3,931,201 A | 1/1976 | Johnston |
| 4,376,646 A | 3/1983 | Rohr et al. |
| 6,333,296 B1 | 12/2001 | Pulman et al. |
| 7,538,072 B2 * | 5/2009 | Mito ...................... A01D 91/04  504/243 |
| 2003/0008884 A1 | 1/2003 | Gerusz et al. |

FOREIGN PATENT DOCUMENTS

| EP | 1122244 B1 | 9/2004 |
| JP | S50101534 A | 8/1975 |
| JP | S56147759 A | 11/1981 |
| JP | 2001519783 A | 10/2001 |
| JP | 2002155061 A | 5/2002 |
| WO | 2006065479 A2 | 6/2006 |
| WO | 2007088996 A1 | 8/2007 |

OTHER PUBLICATIONS

English Translation of International Preliminary Report on Patentability dated Feb. 26, 2019 in International Application No. PCT/JP2017/030248.
English Translation of International Search Report dated Oct. 10, 2017 in International Application No. PCT/JP2017/030248.
Office Action dated Aug. 15, 2020 in AU Application No. 2017316909.
Office Action dated Nov. 24, 2020 in IN Application No. 201917008170

* cited by examiner

*Primary Examiner* — John Pak
(74) *Attorney, Agent, or Firm* — Panitch Schwarze Belisario & Nadel LLP

(57) ABSTRACT

A compound represented by formula (1) is described:

The compound has an excellent efficacy for controlling weeds, and is thus useful as an active ingredient for an agent for controlling weeds.

3 Claims, No Drawings

1-ACETYL-3-PHENYL UREA COMPOUND, AND USE THEREOF

CROSS-REFERENCE TO RELATED APPLICATION

This application is a Section 371 of International Application No. PCT/JP2017/030248, filed Aug. 24, 2017, which was published in the Japanese language on Mar. 1, 2018, under International Publication No. WO 2018/038190 A1, which claims priority under 35 U.S.C. 119(b) to Japanese Application No. 2016-165424 filed on Aug. 26, 2016, the disclosures of which are incorporated herein by reference in their entireties.

TECHNICAL FIELD

The present invention is related to a 1-acetyl-3-phenyl urea compound and a use of the same.

BACKGROUND ART

Patent document 1 describes N-[4-chloro-2-fluoro-5-{2-(ethoxycarbonyl)methoxy-3-pyridyloxy}phenyl]acetamide.

CITATION LIST

Patent Document

Patent Document 1: EP patent No. 1122244 B2

SUMMARY OF THE INVENTION

Problems to be Solved by Invention

An object of the present invention is to provide a compound having an excellent efficacy for controlling weeds.

Means to Solve Problems

The present inventor has intensively studied to solve the problems, and as a result, he found out that a compound represented by the following formula (1) has an excellent control efficacy on weeds.

That is, the present invention includes the followings.
[1] A compound represented by formula (1):

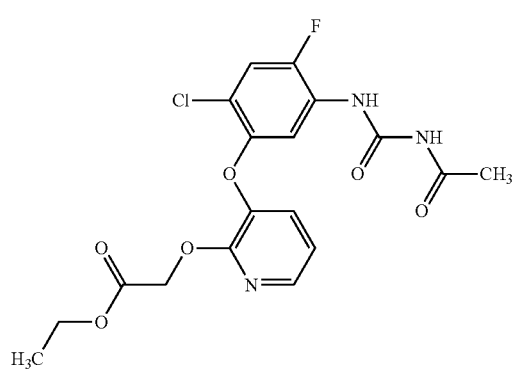

(1)

(hereinafter, referred to as "Compound of the present invention" or "Present compound").

[2] A herbicide comprising the compound described in [1](hereinafter, referred to as "Herbicide of the present invention" or "Present herbicide").

[3] A method for controlling a weed which comprises applying the compound described in [1] to the weed or soil where the weed is growing.

[4] Use of the compound described in [1] to control a weed.

Effect of Invention

The compound of the present invention has an excellent efficacy for controlling weeds, and is thus useful as an active ingredient for a herbicide.

MODE FOR CARRYING OUT THE INVENTION

The herbicide of the present invention comprises a compound of the present invention and an inert carrier. Examples of the inert carrier include a solid carrier and a liquid carrier. The herbicide of the present invention is usually prepared by further adding the other auxiliary agents for formulation such as surfactants, stickers, dispersers, and stabilizers, to formulate into wettable powders, water dispersible granules, suspension concentrates, granules, dry flowables, emulsifiable concentrates, aqueous solutions, oil solutions, smoking agents, aerosols, microcapsules and the others. In the herbicide of the present invention, the compound of the present invention is contained in a range of usually 0.1 to 80% by weight.

Examples of the solid carrier include fine powders or granules of clays (for example, kaolin clay, diatomaceous earth, synthetic hydrated silicon oxides, Fubasami clay, bentonite, or acid white clay), talcs, other inorganic minerals (for example, sericite, quartz powders, sulfur powders, active carbon, calcium carbonate or hydrated silica). Examples of the liquid carrier include water; alcohols (for example, methanol or ethanol); ketones (for example, acetone or methyl ethyl ketone); aromatic hydrocarbons (for example, toluene, xylene, ethyl benzene, or methylnaphthalene); aliphatic hydrocarbons (for example, n-hexane, cyclohexane or kerosene); esters (for example, ethyl acetate or butyl acetate); nitriles (for example, acetonitrile or isobutyronitrile); ethers (for example, diisopropyl ether); and amides (for example, dimethylformamide or dimethylacetamide).

Examples of the surfactants include alkyl sulfates, alkyl sulfonates, alkyl aryl sulfonates, alkyl aryl ethers and polyoxyethylenated compounds thereof, polyoxyethylene glycol ethers, polyhydric alcohol esters, and sugar alcohol derivatives.

Examples of the other auxiliary agents for formulation include a binder and a dispersant. Specific examples include casein, gelatin, polysaccharides (for example, starch, gum arabic, cellulose derivatives or alginic acid), lignin derivatives, bentonite, sugars, water-soluble synthetic polymers (for example, polyvinyl alcohol, polyvinyl pyrrolidone or polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), plant oil, mineral oil, fatty acid and the others.

A method for controlling weeds of the present invention comprises a step of applying an effective amount of a compound of the present invention to weeds or soil where weeds are growing or will grow. In the method for controlling weeds of the present invention, usually, the compound of the present invention is used as a herbicide of the present invention.

Examples of the method of applying the compound of the present invention include a method of applying the present compound to stems and leaves of weeds, a method of applying the present compound to a surface of soil where weeds are growing or will grow, a method of incorporating the present compound into soil where weeds are growing, and a method of applying the present compound to a surface water of paddy field that an area where weeds are growing or will grow is flooded.

Examples of the weeds which can be controlled by the present compound include the following weeds, but are not limited thereto.

Urticaceae weeds: *Urtica urens*;

Polygonaceae weeds: *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius*, and *Rumex acetosa*;

Portulacaceae weeds: *Portulaca oleracea*;

Caryophyllaceae weeds: *Stellaria media, Stellaria aquatica, Cerastium holosteoides, Cerastium glomeratum, Spergula arvensis*, and *Silene gallica*;

Molluginaceae weeds: *Mollugo verticillata*;

Chenopodiaceae weeds: *Chenopodium album, Chenopodium ambrosioides, Kochia scoparia, Salsola kali*, and *Atriplex* spp;

Amaranthaceae weeds: *Amaranthus retroflexus, Amaranthus viridis, Amaranthus lividus, Amaranthus spinosus, Amaranthus hybridus, Amaranthus palmeri, Amaranthus rudis, Amaranthus patulus, Amaranthus tuberculatos, Amaranthus blitoides, Amaranthus deflexus, Amaranthus quitensis, Alternanthera philoxeroides, Alternanthera sessilis*, and *Alternanthera tenella*;

Papaveraceae weeds: *Papaver rhoeas*, and *Argemone mexicana*;

Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymus*, and *Arabidopsis thaliana*;

Capparaceae weeds: *Cleome affinis*;

Fabaceae weeds: *Aeschynomene indica, Aeschynomene rudis), Sesbania exaltata, Cassia obtusifolia, Cassia occidentalis, Desmodium tortuosum, Desmodium adscendens, Desmodium illinoense, Trifolium repens, Pueraria lobata, Vicia angustifolia, Indigofera hirsuta, Indigofera truxillensis*, and *Vigna sinensis*;

Oxalidaceae weeds: *Oxalis corniculata, Oxalis strica*, and *Oxalis oxyptera*;

Geraniaceae weeds: *Geranium carolinense*, and *Erodium cicutarium*;

Euphorbiaceae weeds: *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis*, and *Ricinus communis*;

Malvaceae weeds: *Abutilon theophrasti, Sida rhombifolia, Sida cordifolia, Sida spinosa, Sida glaziovii, Sida santaremnensis, Hibiscus trionum, Anoda cristata*, and *Malvastrum coromandelianum*;

Onagraceae weeds: *Ludwigia epilobioides, Ludwigia octovalvis, Ludwigia decurre, Oenothera biennis*, and *Oenothera laciniata*;

Sterculiaceae weeds: *Waltheria indica*;

Violaceae weeds: *Viola arvensis*, and *Viola tricolor*;

Cucurbitaceae weeds: *Sicyos angulatus, Echinocystis lobata*, and *Ibmordica charantia*;

Lythraceae weeds: *Ammannia multiflora, Ammannia auriculata, Ammannia coccinea, Lythrum salicaria*, and *Rotala indica*;

Elatinaceae weeds: *Elatine triandra*, and *Elatine californica*;

Apiaceae weeds: *Oenanthe javanica, Daucus carota*, and *Conium maculatum*;

Araliaceae weeds: *Hydrocotyle sibthorpioides*, and *Hydrocotyle ranunculoides*;

Ceratophyllaceae weeds: *Ceratophyllum demersum*;

Cabombaceae weeds: *Cabomba caroliniana*;

Haloragaceae weeds: *Myriophyllum aquaticum, Myriophyllum verticillatum*, and Water-milfoils (for example, *Myriophyllum spicatum*, and *Myriophyllum heterophyllum*);

Sapindaceae weeds: *Cardiospermum halicacabum*;

Primulaceae weeds: *Anagallis arvensis*;

Asclepiadaceae weeds: *Asclepias syriaca*, and *Ampelamus albidus*;

Rubiaceae weeds: *Galium aparine, Galium spurium* var. *echinospermon, Spermacoce latifolia, Richardia brasiliensis*, and *Borreria alata*;

Convolvulaceae weeds: *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides*, and *Jacquemontia tamnifolia*;

Boraginaceae weeds: *Myosotis arvensis*;

Lamiaceae weeds: *Lamium purpureum, Lamium amplexicaule, Leonotis nepetaefolia, Hyptis suaveolens, Hyptis lophanta, Leonurus sibiricus*, and *Stachys arvensis*;

Solanaceae weeds: *Datura stramocnium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata*, and *Nicandra physaloides*;

Scrophulariaceae weeds: *Veronica hederaefolia, Veronica persica, Veronica arvensis, Lindernia procumbens, Lindernia dubia, Lindernia angustifolia, Bacopa rotundifolia, Dopatrium junceum*, and *Gratiola japonica*;

Plantaginaceae weeds: *Plantago asiatica, Plantago lanceolata, Plantago major*, and *Callitriche palustris*;

Asteraceae weeds: *Xanthium pensylvanicum, Xanthium occidentale, Xanthium italicum, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza canadensis, Ambrosia artemisiaefolia, Ambrosia trifida, Bidens tripartita, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Mlampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium* hysterophorus, Siegesbeckia orientalis, Soliva sessilis, Eclipta prostrata, Eclipta alba, and Centipeda minima;

Alismataceae weeds: Sagittaria pygmaea, Sagittaria trifolia, Sagittaria sagittifolia, Sagittaria montevidensis, Sagittaria aginashi, Alisma canaliculatum, and Alisma plantago aquatica;

Limnocharitaceae weeds: Limnocharis flava;

Hydrocharitaceae weeds: Limnobium spongia, Hydrilla verticillata, and Najas guadalupensis;

Araceae weeds: Pistia stratiotes;

Lemnaceae weeds: Lemna aoukikusa, Spirodela polyrhiza, and Wolffia spp;

Potamogetonaceae weeds: Potamogeton distinctus, and pond weeds (for example, Potamogeton crispus, Potamogeton illinoensis, and Stuckenia pectinata);

Liliaceae weeds: Allium canadense, Allium vineale, and Allium macrostemon;

Pontederiaceae weeds: Eichhornia crassipes, Heteranthera limosa, Mbnochoria korsakowii, and Mbnochorla vaginalis;

Commelinaceae weeds: Commelina communis, Commelina bengharensis, Commelina erecta, and Mirdannia keisak;

Poaceae weeds: Echinochloa crus-galli, Echinochloa crus-galli var formosensis, Echinochloa oryzoides, Echinochloa colona, Echinochloa crus-pavonis, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Poa trivialis, Poa pratensis, Alospecurus aequalis, Alopecurus myosuroides, Avena fatua, Sorghum halepense, Sorghum vulgare, Agropyron repens, Lolium perenne, Lolium rigidum, Bromus catharticus, Bromus sterilis, Bromus japonicus, Bromus secalinus, Bromus tectorum, Hordeum jubatum, Aegilops cylindrica, Phalaris arundinacea, Phalaris minor, Apera spica-venti, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis pilosa, Rhynchelitrum repens, Dactyloctenium aegyptium, Ischaemum rugosum, Isachne globosa, Oryza sativa, Paspalum notatum, Paspalum maritimum, Paspalum distichum, Pennisetum clandestinum, Pennisetum setosum, Rottboellia cochinchinensis, Leptochloa chinensis, Leptochloa fascicularis, Leptochloa filiformis, Leptochloa panicoides, Leersia japonica, Leersia sayanuka, Leersia oryzoides, Glyceria leptorrhiza, Glyceria acutiflora, Glyceria maxima, Agrostis stolonifera, Cynodon dactylon, Dactylis glomerata, Eremochloa ophiuroides, Festuca arundinacea, Festuca rubra, Imperata cylindrica, Miscanthus sinensis, Panicum virgatum, and Zoysia japonica;

Cyperaceae weeds: Cyperus microiria, Cyperus iria, Cyperus compressus, Cyperus difformis, Cyperus flaccidus, Cyperus globosus, Cyperus nipponics, Cyperus odoratus, Cyperus serotinus, Cyperus rotundus, Cyperus esculentus, Kyllinga gracillima, Kyllinga brevifolia, Fimbristylis miliacea, Fimbristylis dichotoma, Eleocharis acicularis, Eleocharis kuroquwai, Schoenoplectus hotarui, Schoenoplectus juncoides, Schoenoplectus wallichii, Schoenoplectus mucronatus, Schoenoplectus triangulatus, Schoenoplectus nipponicus, Schoenoplectus triqueter, Bolboschoenus koshevnikovii, and Bolboschoenus fluviatilis;

Equisetaceae weeds: Equisetum arvense, and Equisetum palustre;

Salviniaceae weeds: Salvinia natans;

Azollaceae weeds: Azolla japonica, and Azolla imbricata;

Marsileaceae weeds: Marsilea quadrifolia; and

Other weeds: filamentous algae (for example, Pithophora, Cladophora), mosess, liverwort, hornwort, cyanobacteria, bracken, and sucker of parmanent crops (for example, pome fruits, stone fruits, berry fruits, nut fruit, citrus fruit, hop, grapes, and the others).

EXAMPLES

Hereinafter, the present invention is explained in more detail by using Preparation Example and Test Example, however, the present invention should not be limited to these examples.

First, the Preparation Examples are shown.

Preparation Example 1

One point two (1.20) grams of a compound represented by the above-mentioned formula (2) was added to a mixture of 18 mL of acetic acid and 2.7 mL of water, and thereto was added 572 mg of potassium cyanate. The mixture was stirred at room temperature for two hours, and then concentrated under reduced pressure. The obtained residues were subjected to a silica gel column chromatography to give 1.10 g of a compound represented by the above-mentioned formula (3).

$^1$H-NMR (DMSO-$d_6$): δ (ppm): 8.56 (1H, d, J=2.0 Hz), 7.91 (1H, d, J=7.7 Hz), 7.87 (1H, dd, J=5.0, 1.4 Hz), 7.56 (1H, d, J=10.9 Hz), 7.21 (1H, dd, J=7.9, 1.4 Hz), 6.99 (1H, dd, J=7.9, 5.0 Hz), 6.24 (2H, s), 4.93 (2H, s), 4.10 (2H, q, J=7.1 Hz), 1.15 (3H, t, J=7.1 Hz).

Preparation Example 2

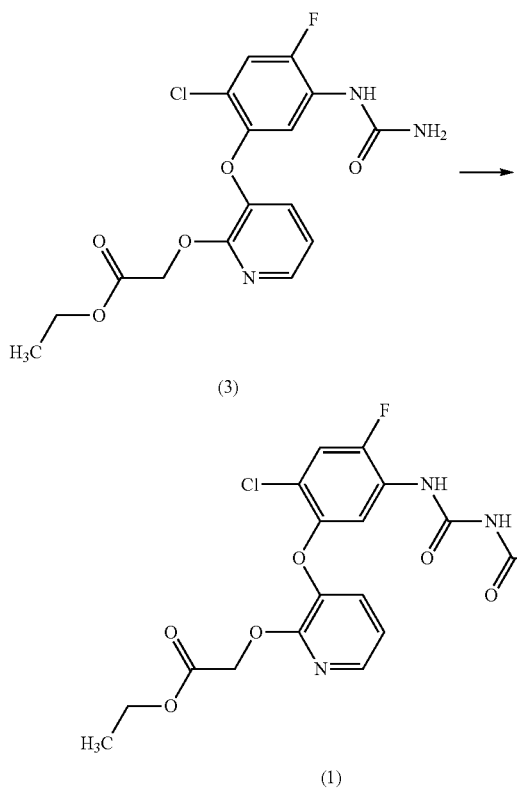

Zero point two eight (0.28) mL of acetyl chloride was added dropwise to a mixture of 0.30 g of the compound represented by formula (3), 0.38 mL of pyridine and 7.0 mL of tetrahydrofuran at room temperature. The mixture was stirred at 40° C. for 6 hours, and then cooled to room temperature. Water was added to the resulting mixture, and the mixture was extracted with ethyl acetate. The obtained organic layer was washed with saturated brine and dried over anhydrous magnesium sulfate, and concentrated under reduced pressure. The obtained residues were washed with chloroform to give 0.23 g of the compound of the present invention.

$^1$H-NMR (DMSO-$d_6$): δ (ppm): 7.91 (1H, dd, J=4.9, 1.6 Hz), 7.82 (1H, d, J=7.1 Hz), 7.71 (1H, d, J=10.5 Hz), 7.32 (1H, dd, J=8.0, 1.6 Hz), 7.02 (1H, dd, J=8.0, 4.9 Hz), 4.93 (2H, s), 4.10 (2H, q, J=7.1 Hz), 2.08 (3H, s), 1.13 (3H, t, J=7.1 Hz).

ESI-MS (posi): 426 [M+H]$^+$

Next, Test examples are shown below.

Test Example 1: Post-Emergence Treatment Test in a Farmland

Nursery soil was put in a plastic pot measuring 8 cm in diameter and 6.5 cm in height, and in the pot, seeds of *Amaranthus retroflexus* were sown, and then covered with soil of about 0.5 cm thickness, and the plants were grown in a greenhouse. When the *Amaranthus retroflexus* plants were grown to two-leaf stage, a diluted solution containing either the present compound or a compound represented by formula (B) below (which is described in European Patent No. 1122244 B2) (hereinafter, referred to as Compound B) was uniformly sprayed on the whole *Amaranthus retroflexus* plants so that the application rates of the chemicals would be values indicated in Table 1.

Here the diluted solution was prepared by dissolving the present compound or the compound B in dimethylformamide solution containing 2% of Tween 20 (polyoxyethylene sorbitan fatty acid ester) (manufactured by MP Biomedicals Inc.) and then diluting the solution with deionized water.

The *Amaranthus retroflexus* plants that were sprayed with the diluted solution containing the present compound or the compound B were grown in a greenhouse. Nine days after spraying, the efficacy for controlling *Amaranthus retroflexus* plants was observed, thereby examining a herbicidal effect. Here the herbicidal effect was visually observed and evaluated by classifying the effect into 11 stages from 0 (no effect) to 10 (complete kill). The results are shown in Table 1.

The results showed that the present compound showed higher herbicidal effect compared to the compound B.

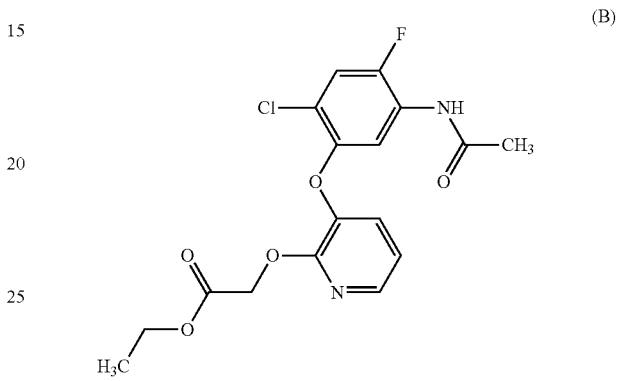

TABLE 1

| | Application Rates of the Chemicals (kg/ha) | Herbicidal Effect |
|---|---|---|
| Present compound | 4 | 8 |
| Compound B | 4 | 1 |

Test Example 2

Inhibitory Activity on Emergence of *Arabidopsis thaliana*

Each well of 24 well microtiter plates was matted with a filter paper, and to the filter paper was added dropwise the solution in which the present compound or the compound B was dissolved in acetone. After air-drying, distilled water was added to each well so that the concentration of the present compound or the compound B in each well would be 8000 ppm. Next, seeds of *Arabidopsis thaliana* were sown into each well containing the present compound or the compound B, followed by putting a lid on each well, and cultivating *Arabidopsis thaliana* under the condition that a cultivation at 25° C. under lighting for 16 hours and a successive cultivation at 25° C. under dark for 8 hours were repeated. Seven days after sowing, the inhibitory activity on emergence of *Arabidopsis thaliana* was visually evaluated by classifying the activity into 0 to 100 indices (0: no effect to 100: no emergence). The results are shown in Table 2.

The result showed that the present compound showed higher inhibitory activity compared to the compound B.

TABLE 2

| | Treatment Concentration (ppm) | Inhibitory Activity on Emergence |
|---|---|---|
| Present compound | 8000 | 80 |
| Compound B | 8000 | 30 |

INDUSTRIAL APPLICABILITY

The compound of the present invention has excellent efficacies for controlling weeds, and is useful as an active ingredient for an agent for controlling weeds.

The invention claimed is:

1. A compound represented by formula (1):

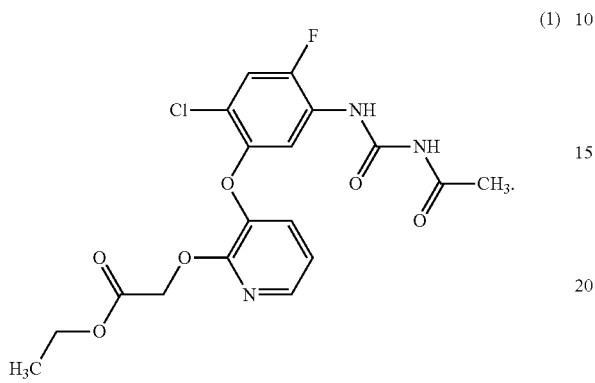

2. A herbicide comprising the compound according to claim 1.

3. A method for controlling a weed which comprises applying the compound according to claim 1 to the weed or soil where the weed is growing.

* * * * *